(12) United States Patent
Wang et al.

(10) Patent No.: US 7,196,197 B2
(45) Date of Patent: Mar. 27, 2007

(54) PROCESS FOR THE PREPARATION OF FLECAINIDE, ITS PHARMACEUTICALLY ACCEPTABLE SALTS AND IMPORTANT INTERMEDIATES THEREOF

(75) Inventors: Zhi-Xian Wang, Brantford (CA); Yuanqiang Li, Brantford (CA); Bhaskar Reddy Guntoori, Brantford (CA)

(73) Assignee: Apotex Pharmachem Inc., Brantford ( * ) Notice: Subject to any disclaimer, the term of this patent is extended or adjusted under 35 U.S.C. 154(b) by 379 days.

(21) Appl. No.: 10/663,836

(22) Filed: Sep. 17, 2003

(65) Prior Publication Data

US 2005/0059825 A1    Mar. 17, 2005

(51) Int. Cl.
*C07D 211/32*    (2006.01)
(52) U.S. Cl. ..................................... 546/233
(58) Field of Classification Search ............... 514/331, 514/329, 428; 546/233
See application file for complete search history.

(56) References Cited

U.S. PATENT DOCUMENTS

| | | | |
|---|---|---|---|
| 3,900,481 A | 8/1975 | Banitt et al. ........... 260/293.77 |
| 4,005,209 A * | 1/1977 | Banitt et al. ................. 514/331 |
| 6,538,138 B1 | 3/2003 | Gutman et al. ............. 546/247 |
| 6,593,486 B2 | 7/2003 | Gutman et al. ............. 558/311 |
| 6,599,922 B2 | 7/2003 | Vigano et al. .............. 514/331 |
| 2003/0032835 A1 | 2/2003 | Vigano et al. | |

FOREIGN PATENT DOCUMENTS

| | | |
|---|---|---|
| GB | 2045760 | 11/1980 |
| WO | WO 99/02498 | 1/1999 |
| WO | WO 02/04419 | 1/2002 |
| WO | WO 02/066413 | 8/2002 |

* cited by examiner

*Primary Examiner*—Taylor Victor Oh
(74) *Attorney, Agent, or Firm*—Francis Ng-Cheng-Hin; Ivor M. Hughes; Neil H. Hughes

(57) ABSTRACT

Process for the preparation of Flecainide, its pharmaceutically acceptable salts and important intermediates thereof that involves the use of the 2-halobenzoic acid and its derivatives as a starting material. The use of this process also allows for the synthesis of a novel intermediate useful in the production of Flecainide. This new process is an inexpensive and efficient process for the manufacture of these compounds.

29 Claims, No Drawings

PROCESS FOR THE PREPARATION OF FLECAINIDE, ITS PHARMACEUTICALLY ACCEPTABLE SALTS AND IMPORTANT INTERMEDIATES THEREOF

A novel process for the preparation of Flecainide, its pharmaceutically acceptable salts and important intermediates thereof.

BACKGROUND

Flecainide acetate, 2,5-bis(2,2,2-trifluoroethoxy)-N-(2-piperidylmethyl)benzamide acetate (I), is a drug for the treatment of arrhythmia. It and its neutral base are described in U.S. Pat. No. 3,900,481.

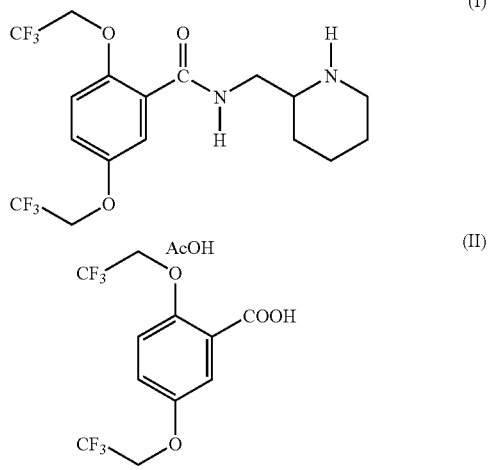

A key intermediate for the synthesis of Flecainide and its pharmaceutically acceptable salts is 2,5-bis(2,2,2-trifluoroethoxy)benzoic acid (II). One prior method for the preparation of this intermediate, disclosed in British patent No. GB 2045760, is a multistep process which comprises the preparation of 1,4-bis(2,2,2-trifluoroethoxy)benzene from hydroquinone using the very expensive reagent trifluoroethyltriflate ($CF_3CH_2OSO_2CF_3$). 1,4-bis(2,2,2-trifluoroethoxy)benzene is then converted to 2,5-bis(2,2,2-trifluoroethoxy)benzoic acid (II) through a multistep process. An alternative method described in the same patent begins from 1,4-dibromobenzene, which is then condensed with more than 8 equivalents of 2,2,2-trifluoroethanol, to furnish the 1,4-bis(2,2,2-trifluoroethoxy)benzene intermediate. 2,5-bis(2,2,2-trifluoroethoxy)benzoic acid (II) is also be prepared starting from 1-bromo-4-fluorobenzene (PCT WO 02/066413) or from 2-bromo-5-chlorobenzoic acid (PCT WO 99/02498). All these approaches have limited commercial utility due to the cost of the reagents and the necessity for specialized equipment.

The method disclosed in British patent No. GB 2045760 for the preparation of the Flecainide base starts from 2,5-bis(2,2,2-trifluoroethoxy)benzoic acid which is converted to its acid chloride and reacts either with 2-(aminomethyl)piperidine to form Flecainide in one step or with 2-(aminomethyl)pyridine, followed by catalytic hydrogenation of the pyridine ring, to form Flecainide base in two steps. The disadvantage of the one step process is that the acid chloride reacts non-selectively with both nitrogen atoms of the 2-(aminomethyl)piperidine, resulting in a mixture of the two acylated isomers.

Other preparations of Flecainide base are disclosed in WO 99/02498 and US2003/0032835. The process disclosed in WO 99/02498 starts from the cyanomethyl ester of 2,5-bis(2,2,2-trifluoroethoxy)benzoic acid, which selectively reacts with the primary amino group of 2-(aminomethyl)piperidine to furnish Flecainide. US 2003/032835 discloses a procedure which involves converting 2,5-bis(2,2,2-trifluoroethoxy)benzoic acid to its activated 2,2,2-trifluoroethyl ester which then selectively reacts with the primary amino group of 2-(aminomethyl)piperidine to furnish Flecainide. Although activated esters of this type can be used for the formation of Flecainide, the reagents required to prepare them are expensive on the industrial scale. Moreover, the resulting cyanomethanol and 2,2,2-trifluoroethanol by-products are highly toxic. Esters from less expensive, non-toxic and readily available alcohols are still desired for commercial purposes. Based on the above deficiencies, a new process overcoming these deficiencies was required.

SUMMARY OF THE INVENTION

It is an object of this invention to provide a novel commercial process for the preparation of Flecainide base, its acetate salt or other pharmaceutically acceptable salts, starting from commercially available and inexpensive halobenzoic acids of formula III, where $X^1$ is F, Cl, Br, or I, and $R^1$ is selected from H, alkali metal, or a $C_1$ to $C_9$ alkyl group.

Scheme 1 outlines the method of preparation of Flecainide. The method includes the following advantages:
1) begins from the inexpensive and readily available 2-halobenzoic acid;
2) high selectivity in the halogenation and amide formation steps;
3) high yield;
4) low cost solvents used throughout; and
5) amendable for large scale production and does not require specialized equipment.

Scheme 1

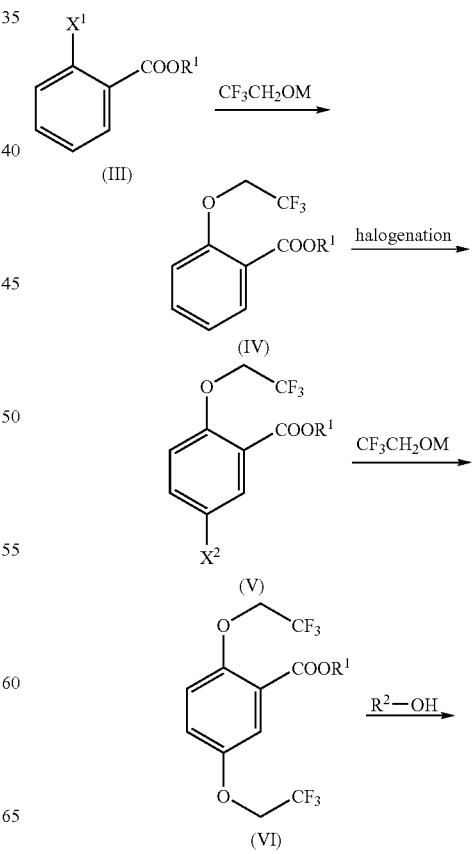

3

-continued

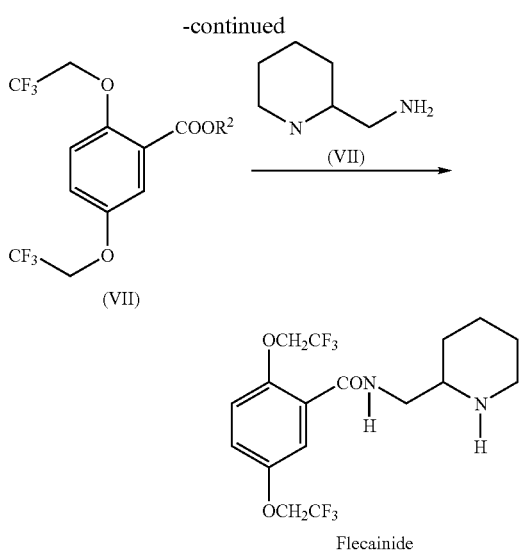

(VII)

Flecainide

It is also an object of this invention to provide a process for the preparation of the key intermediate 2,5-bis(2,2,2-trifluoroethoxy)benzoic acid and it derivatives of the formula VI beginning with the inexpensive starting material of the formula III, where $X^1$ is F, Cl, Br, or I, and $R^1$ is selected from H, alkali metal, or a $C_1$ to $C_9$ alkyl group. Reaction of the starting material of formula III with 2,2,2-trifluoroethanol or any of its suitable derivatives in the presence of a base and a suitable catalyst such as a copper type catalyst provides compounds of the formula IV in high yield (e.g., 80 to 90%). Other suitable catalysts include the palladium and nickel types.

Compounds of formula IV can be converted to 5-halo substituted compounds of formula V by selective halogenation in the 5-position of the aromatic ring in near quantitative yield. A second coupling between the halogen compound (V) and trifluoroethanol or any of its suitable derivatives in the presence of base and a suitable catalyst such as a copper type catalyst provides compounds of formula VI in high yield, where $R^1$ is selected from H, alkali metal or a $C_1$ to $C_9$ alkyl group.

It is also an object of this invention to provide a process for the production of Flecainide from 2-(aminomethyl) piperidine and the compounds of the formula VII, where $R^2$ is selected from $C_1$ to $C_9$ alkyl group, aryl groups, succinimidyl and the like, more preferably $R^2$ is selected methyl, ethyl, benzyl, phenyl, and the like.

It is yet another object of the present invention to make and use the intermediate 5-bromo-2-(2,2,2-trifluoroethyoxy) benzoic acid to manufacture Flecainide.

Surprisingly we have discovered that the simple esters of 2,5-bis(2,2,2-trifluoroethoxy)-benzoic acid such as methyl, ethyl and benzyl esters can selectively react with the primary amino group of 2-(aminomethyl)piperidine to produce Flecainide with high yield and high purity. The alcohols used to form those benzoates are inexpensive, readily commercially available and have relatively low toxicity.

DETAILED DESCRIPTION OF THE INVENTION

In one aspect of the present invention, compounds of formula VI are prepared from the compounds of formula III as the starting material.

4 a) Conversion of 2-halo compounds of formula III to 2-(2,2,2-trifluoroethoxy) substituted compounds of the formula IV (Scheme 2)

As illustrated in Scheme 2, compounds of formula III are reacted with an alkali or alkaline earth metal 2,2,2-trifluoroethoxide, which can be pre-prepared or generated in situ from 2,2,2-trifluoroethanol and a base, in the presence of a suitable catalyst such as a copper, palladium or nickel containing catalyst in a polar solvent. Compounds of formula III are compounds where $X^1$ is selected from F, Cl, Br and I and $R^1$ is selected from H, alkali metals, aryl, and a $C_1$ to $C_9$ alkyl group. The alkali or alkaline earth metal ion M can be sodium ion, potassium ion, calcium ion or lithium ion. The preferable solvents are dipolar aprotic solvents, such as N,N-dimethylformamide, 1-methyl-2-pyrrolidinone, dimethyl sulfoxide, methylethylpyridine. The bases used to deprotonate the 2,2,2-trifluoroethanol include sodium, sodium hydride, sodium amide, sodium and potassium alcoholates, lithium hydroxide, sodium hydroxide, potassium hydroxide and calcium hydroxide. Among them, sodium and sodium hydride were used in similar transformations in the prior art, but they react violently with alcohols and water, and generate hydrogen gas, which is a highly flammable and explosive gas. Reagents of this type are therefore unsafe for large-scale production. In the present invention, preferable bases which overcome the deficiencies of the prior art include sodium methoxide, sodium isopropoxide, sodium tert-butoxide, potassium tert-butoxide, and the like. The most preferable base is potassium tert-butoxide. Compared to sodium metal and sodium hydride, they are much safer for handling in large scale. They are also readily commercially available, and produce the product in high yield and purity. Such suitable catalysts for this transformation are preferably copper-containing catalysts that can include cupric chloride, cupric bromide, cupric iodide, cuprous chloride, cuprous bromide, cuprous iodide, copper (I) oxide, copper (II) oxide, and copper-zinc alloy. The reaction may be performed at temperatures between 0° C. to 200° C., preferably between 80° C. to 120° C.

Scheme 2

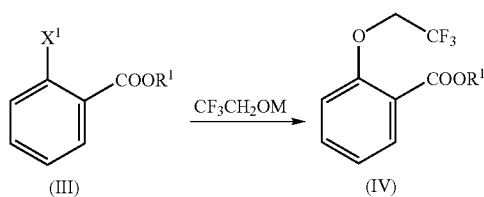

b) Conversion of compounds of formula IV to 5-halo substituted compounds of the formula V (Scheme 3)

The compounds of formula IV are halogenated selectively at the 5-position to provide compounds of formula V, where $X^2$ is selected from Cl, Br or I. This reaction may be performed in the presence of a Lewis acid catalyst. The halogenation reagent may be any of the normally anticipated reagents used for halogenation reactions such as chlorine, N-bromosuccinimide, bromine, N-iodosuccinimide, or iodine. Examples of preferable Lewis acids include, but are not limited to, zinc chloride, zinc bromide, iron, iron chloride, aluminum chloride, aluminum bromide, and boron trifluoride etherate. More preferably, this transformation is performed with bromine and a Lewis acid such as aluminum chloride or iron chloride, due to the fact that they afford high selectivity and resulting in high yield. They are also readily available on an industrial scale and are relatively inexpensive. The solvents may be nonpolar hydrocarbon based, for instance, hexane, heptane, octane, cyclohexane, or polar solvents, for instance, N,N-dimethylformamide, dichloromethane, 1,2-dichloroethane, dimethyl sulfoxide, acetonitrile, tetrahydrofuran, acetic acid and ethyl acetate. Preferable solvents are dichloromethane and 1,2-dichloroethane. The reaction is carried out at temperature between −20° C. to 80° C., preferably between 0° C. to 20° C.

Scheme 3

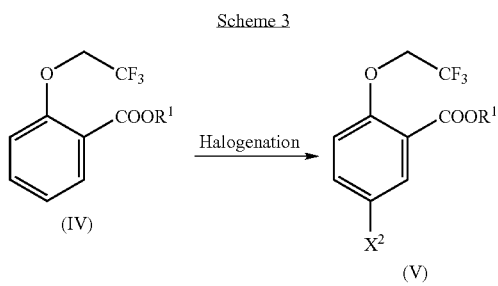

c) Conversion of 5-halo substituted compounds of formula V to compounds of formula VI (Scheme 4)

Compounds of formula V can be converted to compounds of formula VI under similar conditions as described in step a) above, where reaction of the substrate with 2,2,2-trifluoroethanol or any of its suitable derivatives in the presence of a strong base and a suitable catalyst such as a copper, palladium or nickel containing catalyst in an aprotic solvent occurs. The alkali or alkaline earth metal ion M can be sodium ion, potassium ion, calcium ion or lithium ion. The preferable solvents are dipolar aprotic solvents, such as N,N-dimethylformamide, 1-methyl-2-pyrrolidinone, dimethyl sulfoxide. The bases used to deprotonate the 2,2,2-trifluoroethanol include sodium, sodium hydride, sodium amide, sodium and potassium alcoholates, lithium hydroxide, sodium hydroxide, potassium hydroxide and calcium hydroxide. Among them, sodium and sodium hydride were used for similar transformations in the prior art, but they react violently with alcohols and water, generating hydrogen gas, which is a highly flammable and explosive gas, thereby making these bases unsuitable for large-scale production. In the present invention, the preferable bases include sodium methoxide, sodium isopropoxide, sodium tert-butoxide, potassium tert-butoxide and the like. Compared to sodium metal and sodium hydride, they are much safer for handling on industrial scale. They are also readily commercially available, as well as produce the product in high yield and purity. The preferable catalysts are copper-containing catalysts that include cupric chloride, cupric bromide, cupric iodide, cuprous chloride, cuprous bromide, cuprous iodide, copper (I) oxide, copper (II) oxide, and copper-zinc alloy. The reaction may be performed at temperatures between 0° C. to 200° C., preferably between 80° C. to 120° C.

Scheme 4

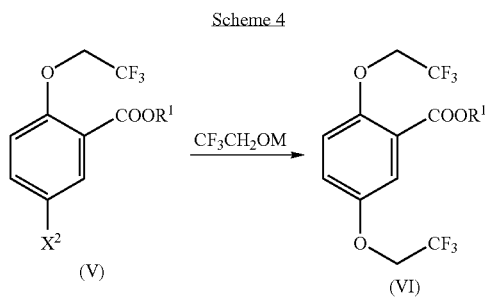

Conversion of Compounds of the Formula VI to Compound of Formula VII (Scheme 5)

Compounds of formula VI may be converted to Flecainide directly by selective amidation of 2-(aminomethyl)piperidine. Compounds of formula VI can also be converted to a new ester of formula VII by reaction with a hydroxyl compound $R^2$—OH. The preferable methods of this transformation include conventional esterification, transesterification, and activation of the acid, for instance by conversion to its acid chloride followed by reacting with a hydroxyl compound $R^2OH$. These transformations are well known to those skilled in the art. The $R^2$ is selected from $C_1$ to $C_9$ alkyl group, aryl groups, succinimidyl and the like. More preferably $R^2$ is selected from methyl, ethyl, benzyl, phenyl, and the like because the alcohols used to prepare these esters are inexpensive, readily commercially available and are relatively non-toxic. The simple benzoates selectively react with the primary amino group of 2-(aminomethyl)piperidine (VIII) to form Flecainide in high yield and purity under the conditions of the present invention.

Scheme 5

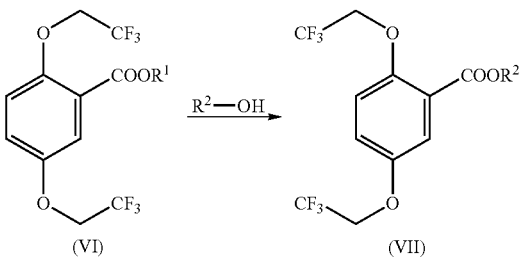

The compounds of formula VI or VII are converted to Flecainide, as Flecainide base or pharmaceutically acceptable salts thereof, by selectively coupling at the primary amino group of 2-(aminomethyl)piperidine. The reaction is mainly dependant upon the solvents, temperature, concentration, and the ratio of the substrates.

The reaction occurs in the absence or in the presence of solvent. The solvents may be aromatic, aliphatic, or cycloaliphatic solvents, from five to ten carbons or ethers from four to ten carbons, for example, hexane, heptane, cyclohexane, toluene, xylenes, diethyleneglycol dimethyl ether (diglyme), 1,2-dimethoxyethane (glyme), acetonitrile, methylene chloride, or tetrahydrofuran, more preferably toluene and xylenes. The reaction temperature range is between 0° C. to 150° C., more preferably is between 50° C. to 120° C. The molar ratio between the benzoate and the piperidine is 1:1 to 1:2, most preferably is 1:1 to 1:1.5.

The Flecainide base obtained by crystallization from the reaction base is easily converted into pharmaceutically acceptable salts via salt-forming reactions well known in the art.

The following non-limiting examples illustrate the process in producing Flecainide base or its pharmaceutically acceptable salts by the process of the present invention.

EXAMPLE 1

Preparation of 2-(2,2,2-trifluoroethoxy)benzoic acid

To a solution of 2,2,2-trifluoroethanol (40.0 g) and DMF (100 ml) was added sodium tert-butoxide (23.0 g) at 0° C. The solution was stirred at 20 to 25° C. for 1 hour at which point 2-chlorobenzoic acid (25.0 g) was added followed by cupric bromide (2.0 g). The mixture was stirred at 120° C. for 5 hours, cooled to 10° C., and water (30 ml) was added followed by 20% HCl solution (90 ml). The solution was extracted with dichloromethane (3×50 ml). The combined organic layers were washed with water (3×50 ml) and the volume was concentrated to 90 ml. Hexane (150 ml) was added to the residues, and the mixture was concentrated to volume of 120 ml and a further portion of hexane (30 ml) was added. The mixture was heated at 50° C. for 30 minutes and then stirred at room temperature for 1 hour. The solids were filtered to yield the crude product. This material was dissolved in ethyl acetate (50 ml), charcoal (1.7 g) was added and the mixture was stirred at room temperature a further 2 hours. The solution was filtered through Celite™ and crystallized from ethyl acetate/hexane to yield the pure product (30.9 g, yield 88.0%) as a white solid, m.p. 85–86° C.

EXAMPLE 2

Preparation of 5-bromo-2-(2,2,2-trifluoroethoxy)benzoic acid

To a solution of 2-(2,2,2-trifluoroethoxy)benzoic acid (22 g) in methylene chloride (100 ml), was added $AlCl_3$ (13.3 g) at 0° C.followed by bromine (16.0 g, 0.1 mol). The reaction mixture was stirred at 0° C. for 1 hour and then at reflux for 2 hours. The solids were filtered and water (50 ml) and ethyl acetate (50 ml) were added to the filtrate. The aqueous layer was separated and extracted with ethyl acetate (2×60 ml) and the combined organic layers were washed with water (2×60 ml). The organic layer was concentrated under vacuum to dryness and hexane (100 ml) was added and the resulting suspension was stirred at 20 to 25° C. for 1 hour. The mixture was filtered and the cake was rinsed with heptanes (2×20 ml). The damp solids were dried in vacuum at 45° C. for 5–6 hours to give a white solid (28.3 g, yield 94.6%), m.p. 126–128° C.

EXAMPLE 3

Preparation of 2,5-bis(2,2,2-trifluoroethoxy)benzoic acid.

To a solution of 2,2,2-trifluoroethanol (14.7 g) and DMF (125 ml) was added sodium tert-butoxide (12.8 g) at 0° C. The solution was stirred at 20 to 25° C. for 1 hour at which point 5-bromo-2-(2,2,2-trifluoroethoxy)benzoic acid (20 g) was added followed by cupric bromide (2.0 g). The mixture was stirred at 100° C. for 10 hours, cooled to 10° C., and water (30 ml) was added followed by 20% HCl solution (90 ml). The solution was extracted with dichloromethane (3×80 ml), and the combined organic layers were washed with water (3×60 ml). The solution was concentrated to one-third of the original volume and hexane (200 ml) was added. The resulting suspension was stirred at room temperature for 2 hours, filtered and the damp cake was rinsed with hexane (2×40 ml). The damp cake was dried in vacuo at 40° C. for 5 hours to give the product as a white solid (16.02 g, yield 75.3%).

EXAMPLE 4

Preparation of methyl 2,5-bis(2,2,2-trifluoroethoxy)benzoate

A solution of 2,5-bis(2,2,2-trifluoroethoxy)benzoic acid (20 g) and thionyl chloride (15.0 g) in methanol (100 ml) was stirred at 80° C. for 2 hours. The solvents were evaporated under vacuum to give an oil residue. Toluene (100 ml) was added to the residue and the solution was washed with saturated $NaHCO_3$ (30 ml) solution followed by water (3×30 ml). The organic layer was concentrated under reduced pressure to give the product as a white solid (20.5 g, yield 98.0%).

EXAMPLE 5

Preparation of Flecainide

A mixture of methyl 2,5-bis(2,2,2-trifluoroethoxy)benzoate (1.5 g), 2-(aminomethyl)piperidine (0.62 g) in toluene (3 ml) was stirred at reflux for 10 hours. After cooling to room temperature, water (10 ml) was added and two layers solution were separated. The aqueous layer was extracted with toluene (2×10 ml) and the combined organic layers were washed with water (3×10 ml). The organic layer was concentrated under reduced pressure to give Flecainide free base as a white solid (1.63 g, 85%).

EXAMPLE 6

Preparation of Flecainide acetate

To a solution of Flecainide free base (1.5 g) in isopropanol (7.5 ml) was added glacial acetic acid (0.3 g) and the solution was stirred under reflux for 2 hours. The solution was cooled to room temperature and hexane (15 ml) was added and solids began to precipitate. The resulting suspension was stirred at 20–25° C. for 2 hours and the solids were filtered and then rinsed with hexane (2×10 ml). The damp cake was dried in vacuum for 4 hours to give Flecainide acetate as a white solid (1.54 g, Yield 89%).

What is claimed is:

1. Process for the preparation of Flecainide, as Flecainide base or any pharmaceutically acceptable salts thereof, comprising:

preparation of a compound of formula VI

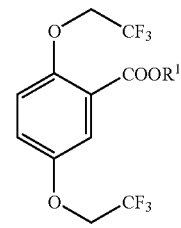

(VI)

wherein $R^1$ is H alkali metal or a $C_1$ to $C_9$ alkyl group; from compounds of formula III

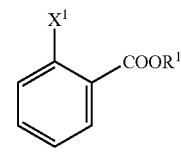

(III)

wherein $X^1$ is F, Cl, Br or I and $R^1$ is H, alkali metal or a $C_1$ to $C_9$ alkyl group;

optional conversion of the compound of formula VI to the ester of formula VII by reacting with a hydroxyl compound $R^2OH$;

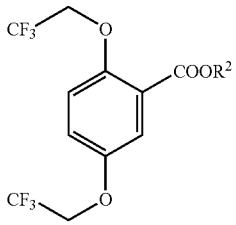

(VII)

wherein $R_2$ is $C_1$ to $C_9$ alkyl group, aryl group or succinimidyl;

amide formation of the compound of formula VI or VII forming flecainide base by reacting with 2-(aminomethyl)piperidine and;

optionally forming a pharmaceutically acceptable salt thereof.

2. Process for the preparation of Flecainide, as Flecainide base or any pharmaceutically acceptable salts thereof, comprising reaction of the compounds formula III with an alkali or alkaline earth metal alkoxide of 2,2,2-trifluoroethanol in the presence of a copper-containing catalyst comprising cupric chloride, cupric bromide, cupric iodide, cuprous chloride, cuprous bromide, cuprous iodide, copper (I) oxide, copper (II) oxide or copper-zinc alloy, in a solvent to form compounds of formula IV;

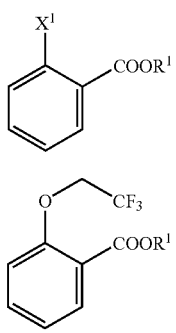

(III)

(IV)

wherein $X^1$ is F, Cl, Br or I and $R^1$ is H, alkali metal or a $C_1$ to $C_9$ alkyl group;

halogenation of the compounds of formula IV to form 5-halo-2-(2,2,2-trifluoroethoxy)benzoic acid derivatives of formula V;

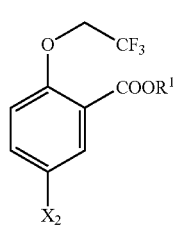

(V)

wherein $X^2$ is Cl, Br, or I and $R^1$ alkali metal or a $C_1$ to $C_9$ alkyl group;

reaction of the compounds of formula V with an alkali or alkaline earth metal alkoxide of 2,2,2-trifluoroethanol in the presence of a copper-containing catalyst comprising cupric chloride, cupric bromide, cupric iodide, cuprous chloride, cuprous bromide, cuprous iodide, copper (I) oxide, copper (II) oxide or copper-zinc alloy in a solvent to form compounds of formula VI;

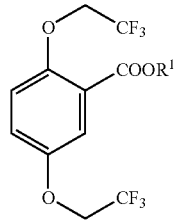

(VI)

wherein $R^1$ is H, alkali metal or a $C_1$ to $C_9$ alkyl group;

optional conversion of the compounds of formula VI to a new ester of formula VII by reacting with hydroxyl compound $R^2OH$;

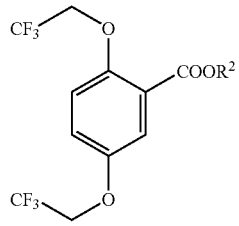

(VII)

wherein $R^2$ is $C_1$ to $C_9$ alkyl group, aryl group or succinimidyl;

selective amide formation by reacting compounds of formula VI or VII with 2-(aminomethyl)piperidine forming flecainide base;

optionally forming a pharmaceutically acceptable salt thereof.

3. The process of claim 2 wherein either solvent comprises a polar solvent.

4. The process of claim 2 wherein the pharmaceutically acceptable salt is the monoacetate salt.

5. The process according to claim 2, wherein the alkali or alkaline earth metal alkoxide of 2,2,2-trifluoroethoxide is sodium, potassium, calcium or lithium 2,2,2-trifluoroethoxide.

6. The process according to claim 2, wherein the alkali or alkaline earth metal alkoxide of 2,2,2-trifluoroethanol is synthesized by reacting 2,2,2-trifluoroethanol with a base selected from potassium tert-butoxide, sodium tert-butoxide, sodium isopropoxide and sodium methoxide.

7. The process according to claim 2, wherein $X^2$ is Br.

8. The process according to claim 2, wherein $R^2$ is selected from methyl, ethyl, benzyl and phenyl.

9. The process according to claim 2, wherein the compound of formula VI or VII is 2,5-bis-(2,2,2-trifluoroethoxy)benzoate.

10. The process according to claim 9 wherein any of the reactions is carried out in aliphatic, cycloaliphatic or aromatic solvents from 5 to 10 carbon atoms or ethers from 4 to 10 carbon atoms.

11. The process according to claim 10, wherein the solvents comprise hexane, heptane, cyclohexane, tetrahydrofuran, 1,2-dimethoxyethane, diethyleneglycol dimethyl ether, toluene, xylene, or acetonitrile.

12. The process according to claim 9, wherein the reaction temperature is between 0° C. to 150° C.

13. The process according to claim 9, wherein the temperature is between 50° C. to 120° C.

14. The process according to claim 9, wherein the molar ratio between 2,5-bis-(2,2,2-trifluoroethoxy)benzoate and 2-aminomethylpiperidine is from 1:1 to 1:2.

15. The process according to claim 14, wherein the molar ratio is from 1:1 to 1:1.5.

16. The process for the preparation of compounds of formula VI;

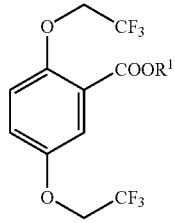

(VI)

wherein R¹ is H, alkali metal or a $C_1$ to $C_9$ alkyl group; from compounds of formula III

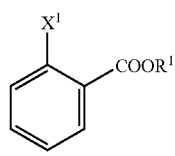

(III)

wherein X¹ is F, Cl, Br or I and R¹ is H, alkali metal or a $C_1$ to $C_9$ alkyl group;
comprising:
reaction of compounds of formula III with an alkali or alkaline earth metal alkoxide of 2,2,2-trifluoroethanol in the presence of a copper-containing catalyst comprising cupric bromide, cupric iodide, cuprous chloride, cuprous bromide, cuprous iodide, copper (I) oxide, copper (II) oxide or copper-zinc alloy, in a solvent to form compounds of formula IV;

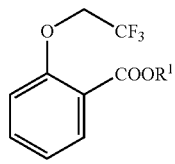

(IV)

wherein R¹ is H, alkali metal or a $C_1$ to $C_9$ alkyl group;
halogenation of the compounds of formula IV to form compounds of formula V;

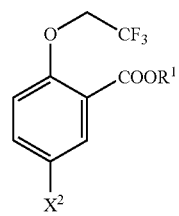

(V)

wherein X² is Cl, Br, or I and R¹ is H, alkali metal or a $C_1$ to $C_9$ alkyl group;
reaction of compounds of formula V with an alkali or alkaline earth metal alkoxide of 2,2,2-trifluoroethanol in the presence of a copper-containing catalyst comprising cupric bromide, cupric iodide, cuprous chloride, cuprous bromide, cuprous iodide, copper (I) oxide, copper (II) oxide or copper-zinc alloy, in a solvent.

17. The process according to claim 16 wherein either solvent comprises a polar solvent.

18. The process according to claim 16, wherein the alkali or alkaline earth metal alkoxide of 2,2,2-trifluoroethoxide is sodium, potassium, calcium or lithium 2,2,2-trifluoroethoxide.

19. The process according to claim 16, wherein the alkali or alkaline earth metal alkoxide of 2,2,2-trifluoroethoxide is synthesized by reacting 2,2,2-triflouroethanol with a base selected from potassium tert-butoxide, sodium tert-butoxide, sodium isopropoxide and sodium methoxide.

20. The process according to claim 16, wherein X² is Br.

21. The process for the preparation of Flecainide from compounds of formula VII,

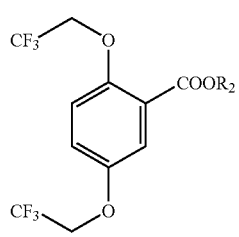

(VII)

wherein R² is methyl, ethyl, propyl, butyl, benzyl, phenyl or succinimidyl;
comprising the selective amide formation by reacting the compound of formula VII with 2-(aminomethyl) piperidine.

22. The process according to claim 21, wherein the reaction is carried out in aliphatic, cycloaliphatic or aromatic solvents from 5 to 10 carbon atoms or ethers from 4 to 10 carbon atoms.

23. The process according to claim 21, wherein the reaction is carried out in solvents and the solvents are selected from hexane, heptane, cyclohexane, tetrahydrofuran, 1,2-dimethoxyethane, diethyleneglycol dimethyl ether, toluene, xylene, acetonitrile.

24. The process according to claim 22, wherein the solvent is toluene or xylene.

25. The process according to claim 21, wherein the reaction temperature is between 0° C. and 150° C.

26. The process according to claim 21, wherein temperature range is between 50° C. and 120° C.

27. The process according to claim 21, wherein the molar ratio between the compound of formula VII and 2-aminomethylpiperidine is from 1:1 to 1:2.

28. The process according to claim 27, wherein the molar ratio is from 1:1 to 1:1.5.

29. 5-Bromo-2-(2,2,2-trifluoroethoxy)benzoic acid.

* * * * *